United States Patent [19]

DeBusk

[11] Patent Number: 5,235,795
[45] Date of Patent: Aug. 17, 1993

[54] SYSTEM FOR THE DELIVERY, STORAGE AND DISPOSAL OF MEDICAL SUPPLIES

[75] Inventor: Autry O. V. DeBusk, Powell, Tenn.

[73] Assignee: DeRoyal Industries, Inc., Powell, Tenn.

[21] Appl. No.: 901,535

[22] Filed: Jun. 19, 1992

Related U.S. Application Data

[63] Continuation of Ser. No. 521,238, May 9, 1990, abandoned.

[51] Int. Cl.⁵ .................. B65B 5/08; B65B 25/00
[52] U.S. Cl. .................................. 53/467; 53/468; 53/474; 53/492; 206/520; 220/254; 220/355; 220/404; 220/908; 414/403; 414/411; 414/786; 588/205; 588/261
[58] Field of Search .............. 220/304, 254, 355, 404, 220/908; 206/366, 520; 423/659; 53/467, 468, 473, 492; 414/403, 411, 786; 588/205, 261

[56] References Cited

U.S. PATENT DOCUMENTS

| D. 218,359 | 8/1970 | Marsh | D49/35 |
|---|---|---|---|
| D. 236,375 | 8/1975 | Moriconi et al. | D55/1 B |
| D. 264,879 | 6/1982 | Baker | D24/99 |
| D. 287,897 | 1/1987 | Hanifl | D34/1 |
| D. 299,578 | 1/1989 | Wilson | D34/25 |
| D. 304,109 | 10/1989 | Hanifl | D34/7 |
| 4,351,539 | 9/1982 | Rodolakis | 280/47.26 |
| 4,420,168 | 12/1983 | Dewing | 280/43.1 |
| 4,453,648 | 6/1984 | Harris et al. | 220/324 |
| 4,488,643 | 12/1984 | Pepper | 206/366 |
| 4,585,138 | 4/1986 | Jonkers | 220/67 |
| 4,637,545 | 1/1987 | Stewart | 232/43.2 |
| 4,779,728 | 10/1988 | Hanifl et al. | 206/366 |
| 4,842,138 | 6/1989 | Sandel et al. | 206/370 |
| 4,874,103 | 10/1989 | Quisenberry et al. | 220/1 T |
| 4,877,150 | 10/1989 | Otto et al. | 206/366 |
| 4,886,164 | 12/1989 | Stein et al. | 206/366 |
| 4,911,294 | 3/1990 | Russo et al. | 220/908 |
| 4,975,019 | 12/1990 | Cate et al. | 220/908 |
| 5,097,950 | 3/1992 | Weiss et al. | 220/908 |
| 5,154,345 | 10/1992 | Shillington | 220/908 |

OTHER PUBLICATIONS

Alexander, Kelly; Medical Waste Disposal Methods: One Hospital's Solution; *Journal of Healthcare Material Management*, vol. 8, No. 2; Feb./Mar. 1990; (4 pages).

Chapnick, Sandi R.; Selecting a Medical Waste Disposal Service; *Journal of Healthcare Material Management*, vol. 8, No. 2; Feb./Mar. 1990; (5 pages).

*Primary Examiner*—Wayne Langel
*Attorney, Agent, or Firm*—Luedeka, Hodges, Neely & Graham

[57] ABSTRACT

A system for the delivery, storage and disposal of medical supplies including a lidded receptacle for receiving the supplies and facilitating their delivery to a use site, such lidded container subsequently being employed in the collection and ultimate disposal of waste medical supplies. The preferred receptacle includes lid means that serves to temporarily close the receptacle when unused medical supplies are held within the receptacle, and that serves the further subsequent function of lockingly closing and sealing the receptacle when waste medical supplies are contained in the receptacle.

6 Claims, 6 Drawing Sheets

SYSTEM FOR THE DELIVERY, STORAGE AND DISPOSAL OF MEDICAL SUPPLIES

This application is a continuation of application Ser. No. 07/521,238 filed May 9, 1990, abandoned.

This invention relates to systems for the delivery, storage and disposal of medical supplies, particularly those medical supplies which are classified as disposable, that is, the supplies are discarded after a single use.

Particularly in the surgical departments of medical institutions and facilities, e.g. surgery centers, doctors offices, etc. it is common practice to maintain in inventory numerous items of medical supplies, commonly sterile in nature, for use in anticipated medical procedures. For example, in the prior art it has not been uncommon that hundreds and even thousands of items of sterile and non-sterile medical supplies are ordered in advance and kept in storage in or near a surgical department of a hospital, etc. Typical items include surgical sponges, drapes, basins, syringes, needles, sutures, and surgical instruments. Many of these items are intended for a single use, following which the used item is discarded. Such items are referred to as disposables. The problems of storage of such items, maintenance of inventory records, and the attendant expenses, have led to the practice of collecting into a grouping, all or many of the disposable medical supplies that are anticipated to be required for a particular surgical procedure, e.g. an appendectomy, packaging such grouping in a manner such that the packaged items can be sterilized after being packaged, sterilizing the package and thereafter storing the sterilized package as a unit. This practice further has led medical suppliers to offer to hospitals and other medical facilities a product known as a "procedural tray". A procedural tray comprises a collection of disposable medical supplies intended for use in a given medical procedure in a package which includes a flat tray and which is sterilized as a unit, such packaging designed to protect the integrity of the sterile nature of the medical supplies contained within the package. Such procedural trays presently are available from several commercial sources and are offered in generic forms, such a wound dressing tray, and/or in customized forms, such as an heart catherization tray for the procedure employed by a particular surgeon. In a particular surgical procedure, it is not uncommon to use one or more generic trays, such as a tray containing table covers, gowns and gloves, plus one or more trays that are customized for the particular surgical procedure. In an effort to reduce the number of trays held in inventory by a surgical facility, it is currently common practice for medical suppliers to maintain the trays in the supplier's warehouse and to deliver to the medical facility those trays that are ordered on relatively short notice.

A major consideration associated with the use of disposable medical supplies, whether prepackaged or not, is how to safely and efficiently dispose of the medical supplies after they have been once used. Recalling that such disposable supplies may include needles and disposable surgical instruments, such as blades, scalpels, etc. and the like, and further recognizing the inherent danger of injury and/or infection should the medical personnel or others handling the used items be accidentally cut, pricked or stuck with an infected used needle, etc., it is immediately obvious that great care must be taken in the handling and disposal of such used items.

Further, in the course of a surgical procedure, it is not uncommon that many of the disposable items will be contaminated with the blood or body fluids of a patient. Physical contact with such blood or fluids, if contaminated with an infectious disease, can expose third parties to such disease. Thus, used medical supplies require special handling commencing immediately following their use and continuing through the ultimate disposal of the items in a manner which ensures the destruction of any potentially contaminating materials without undue exposure of third parties. In certain circumstances, it is further required that the medical waste be converted to a form in which none of the particular items of the waste are recognizable. The procedures which are currently mandated for the proper handling and disposal of used medical supplies are expensive and time-consuming. Current proposed and existing legal and/or regulatory requirements dictate the collection of medical wastes in readily identifiable containers (e.g. distinctive color and identification markings) that provide protection against leakage of liquids from the containers, protection against penetration of the container by needles, scalpels, etc. and protection against inadvertent, or even intentional, opening of the container prior to its ultimate disposal (e.g. protection against container rupture if inadvertently dropped and protection against potential scavenging of the waste items). Further, accountability is required for certain containers of medical waste, especially where the container travels outside a medical facility, such as where the waste is handled by contract waste disposal companies. Importantly, the container itself should not contribute to environmental contamination in the course of its disposal.

Accordingly, it is an object of the present invention to provide a system for the delivery, storage and disposal of medical supplies. It is another object to provide such a system which is particularly safe, efficient and tamper-proof. It is another object to provide such a system which provides a common receptacle for use in the delivery, storage and ultimate disposal of the medical supplies. Other objects and advantages of the invention will be recognized from the description contained herein, including the drawings in which.

In accordance with the present system, medical supplies, commonly pre-sterilized, are held within a rigid lidded receptacle which is suitable for protecting such supplies in the course of their transfer from the manufacturing facility, to the medical facility. Within the medical facility, the products in such receptacle are stored pending their use. The preferred receptacle occupies minimum floor space for storage and therefore can be stored directly in the vicinity of the use site of the supplies. Such use site frequently is an operating room or the like. At the time of their use, the supplies are removed from the receptacle, unpackaged using the normal procedures, and the empty receptacle is placed conveniently near the use site to receive waste products, including the used supplies which originally were delivered in the receptacle. Upon completion of the medical procedure, e.g. surgical operation, and as a part of clean-up, the receptacle is sealed as by means of an interlocking lid which is non-removable other than by destruction of the locking means or by purposeful application of a combination of inordinate forces. Proper labeling may be applied by the end-user to the receptacle to provide for its identification and tracking from the time that it is closed and sealed to its ultimate destruction and/or disposal in accordance with accepted procedures. Preferably, the labeling includes bar coding that is computer-readable for ready and efficient identification of the receptacle. The preferred receptacle includes wheel means so that at all times, and especially upon completion of the sealing of the receptacle, it can readily be transferred from location to location without lifting. As practiced at the particular medical facility, the receptacle of waste is transferred to an inhouse disposal site, such as an incinerator, or to an off-site disposal site. Depending upon the regulations in force with respect to the medical waste in question, the receptacle and its contents may be sterilized, as by radiation, crushed in a grinder or the like to render the individual items of waste unrecognizable and to destroy the receptacle, and thereafter incinerated or disposed of in a landfill.

Figure 1:
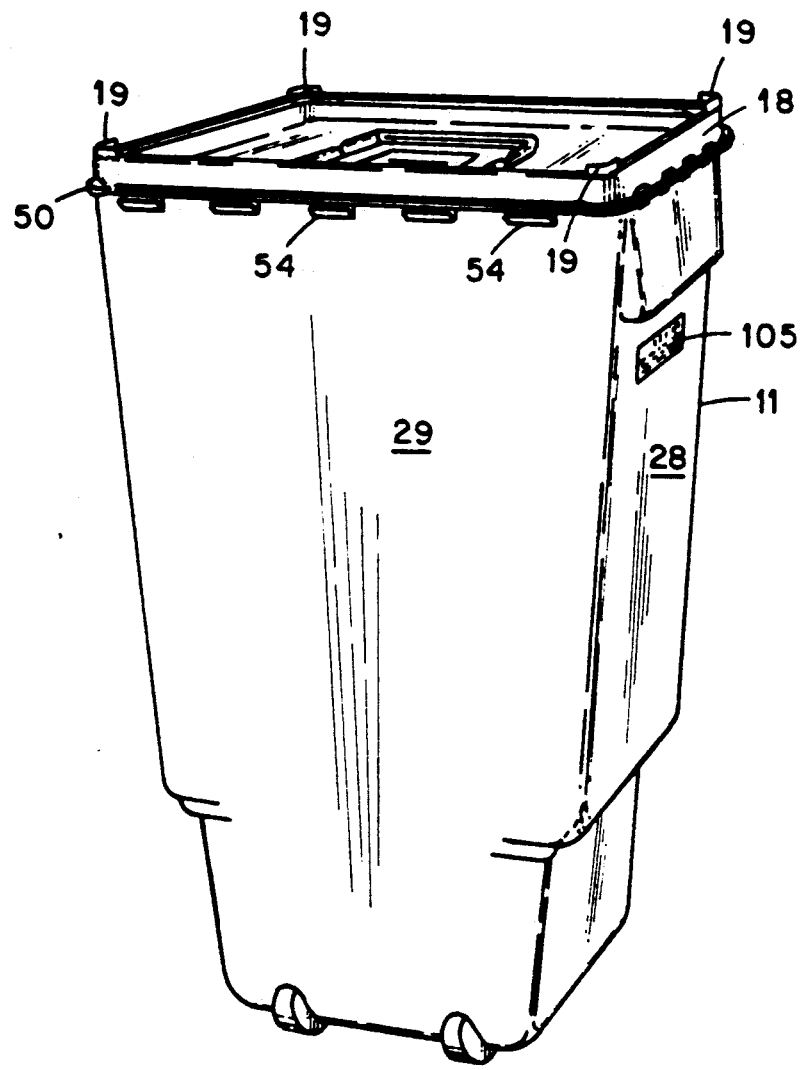
FIG. 1 is a representation of a lidded receptacle suitable for use in the system of the present invention.
Figure 2:
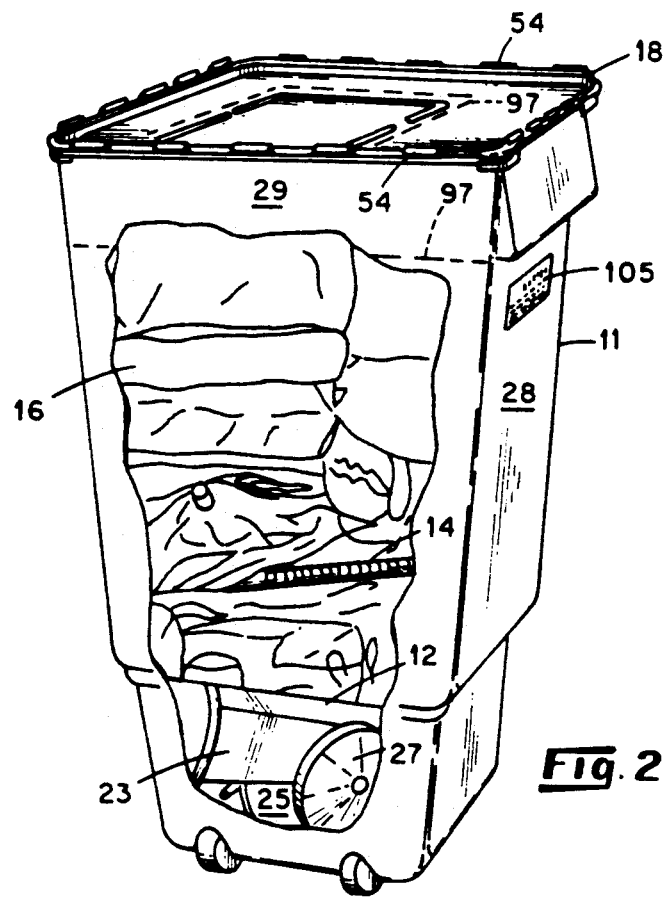
FIG. 2 is a representation of the receptacle of FIG. 1 with a portion of the wall thereof cutaway and depicting typical medical supplies held within the container and ready for use.
Figure 3:
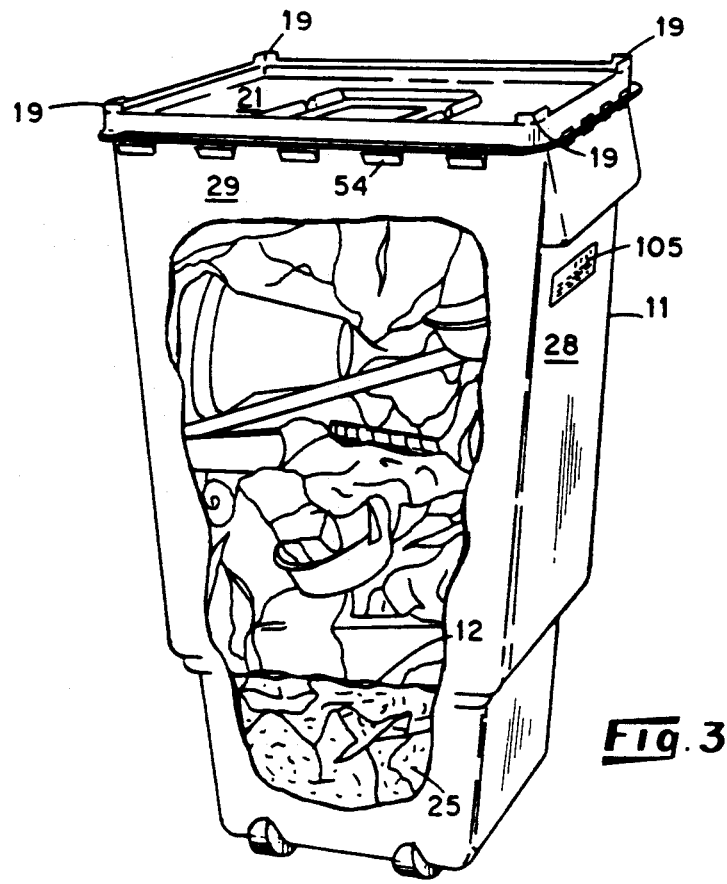
FIG. 3 is a representation of the receptacle of FIG. 1 with a portion of the wall thereof cutaway and depicting typical contents of used medical supplies contained therein and ready for disposal.

A typical lidded receptacle 10 as supplied to a medical facility is depicted in FIGS. 1–3 and includes a receptacle 11 and a lid 18. The depicted receptacle may hold one or more procedural trays 12, 14, and 16, each of which comprises disposable medical supplies such as surgical sponges, syringes, needles and the like. A tray may also contain a quantity of liquid, such as povidone iodide as used in disinfecting the skin of a patient in the area of a surgical procedure. Thus, the receptacle 11 must be sufficiently rigid to be self-supporting, must be liquid-impermeable, and include provision for sealing the receptacle (liquid-tight) following the deposit of used medical supplies therein. The preferred seal prohibits removal of the lid 18 of the receptacle after the seal has been completed, thereby precluding inadvertent or even intentional removal of the lid in the interval between the sealing of the receptacle by the medical personnel who deposit the used supplies therein and the ultimate incineration or other disposal of the receptacle and its contents.

A preferred receptacle 11 is of generally rectangular horizontal cross-section and fabricated from high density polyethylene which is incineratable, producing carbon dioxide and water as byproducts, and a preferred lid 18 is fabricated from polypropylene which also is incineratable, producing carbon dioxide, water and small amounts of carbon monoxide. Conventional plastic fabrication techniques, such as blow molding, may be employed in the fabrication of the receptacle or such as injection molding in the fabrication of the lid 18. The thickness of side walls of the depicted receptacle 11 and of the lid 18 preferably is at least about 3/32 inch, such thickness of either high density polyethylene or polypropylene plastic being sufficient to prevent the incidental penetration thereof by a needle or surgical instrument contained therein. The depicted receptacle 11 includes size walls 26, 28, 29 and 31, a bottom 22 and an open top 24, is about 32" inches high and has a cross-sectional area adjacent its bottom 22 of about 195 in$^2$ and a cross-sectional area adjacent its open top 24 of about 332 in$^2$, thereby providing a generally tapered cross-sectional profile for the receptacle. Whereas such size of the receptacle is preferred to provide maximum storage volume within the receptacle with minimum size "foot print" of the receptacle, other sizes of receptacles may be chosen to provide other advantages.

Figure 4:
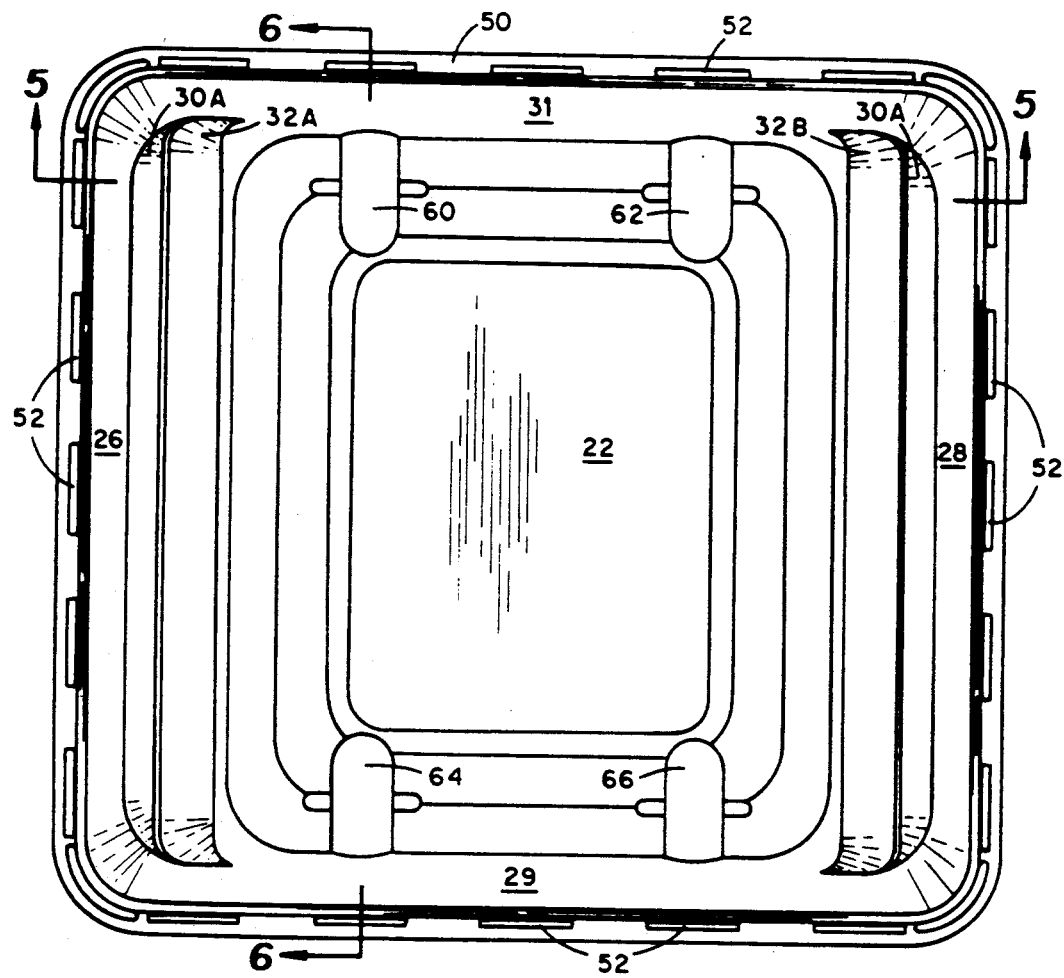
FIG. 4 is a top view of the receptacle of FIG. 1 (unlidded) and depicting various features of the receptacle.
Figure 5:
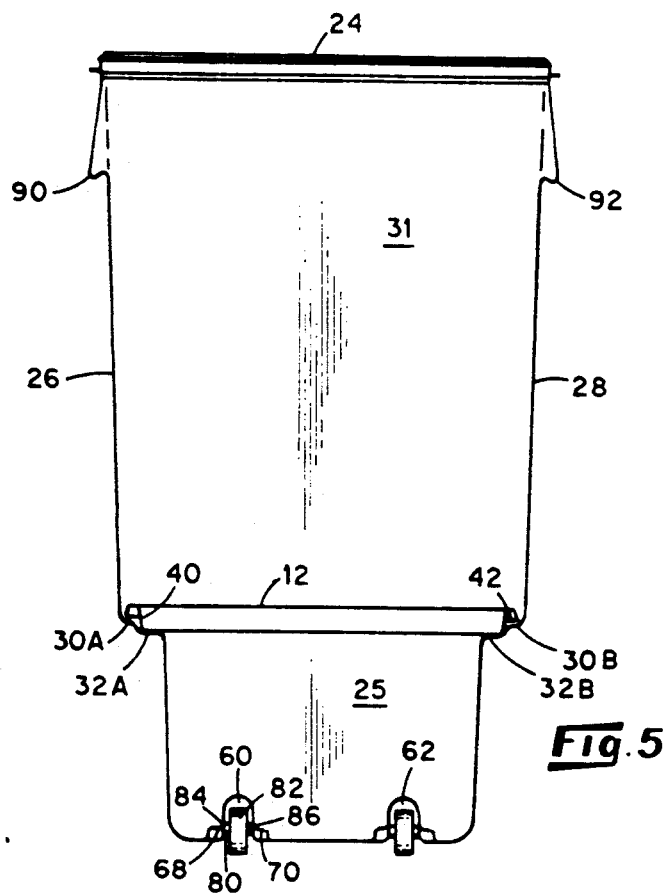
FIG. 5 is a cross-sectional view taken generally along the line 5—5 of FIG. 4.
Figure 8:
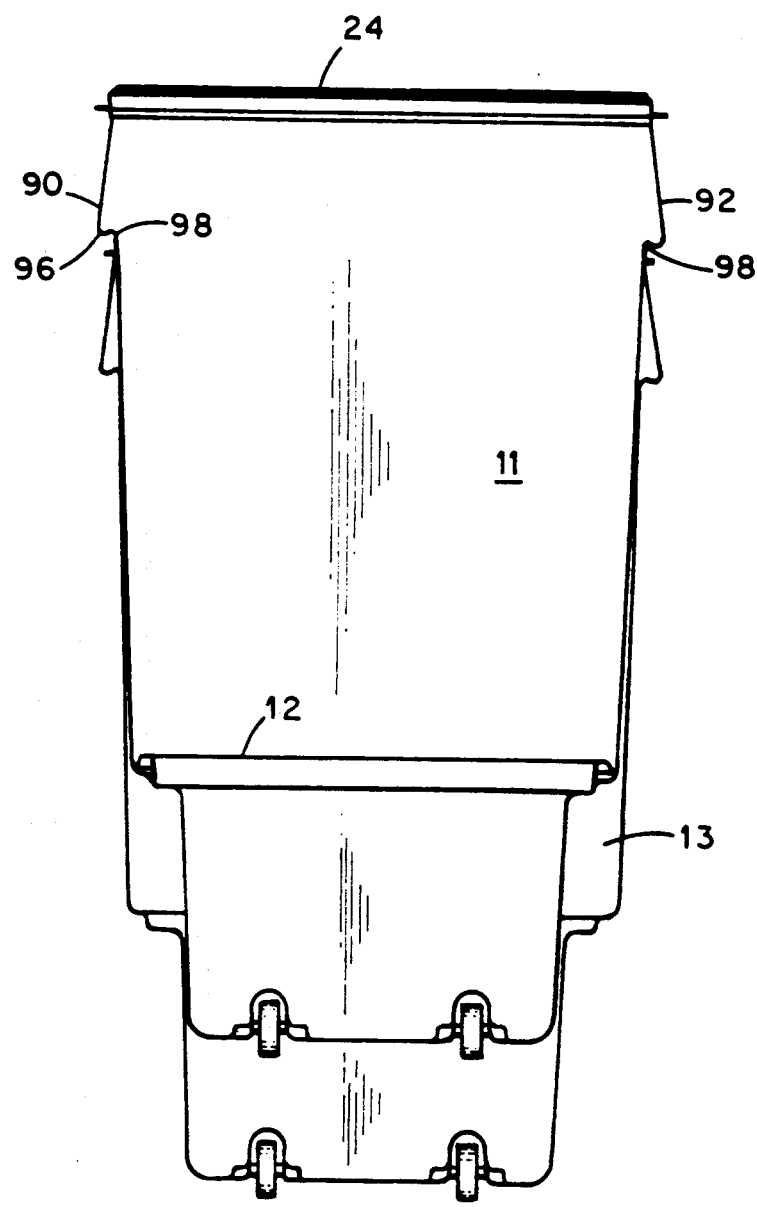
FIG. 8 is a cross-sectional view of two of the receptacles depicted in FIG. 5 as stacked in nested relationship with one another.

As noted and as depicted in FIGS. 4 and 5, in a preferred receptacle 11, the opposite side walls 26 and 28 of the receptacle 11, at a location above the bottom 22 of the receptacle and about ⅛ to ¼ the distance from the bottom of the receptacle to its open top 24, are indented horizontally inwardly of the receptacle to develop first and second sets of ledges 30A and 30B, and 32A and 32B, respectively, on the side walls 26 and 28 of the receptacle 11, the first set of ledges 30A and 30B being at substantially identical horizontal heights above the bottom 22 of the receptacle to establish a first level and the ledges 32A and 32B of the second set of ledges being at substantially identical heights above the bottom of the receptacle to establish a second level that is different from the first level. These ledges 30A, 30B, 32A and 32B serve to receive the ends 42 and 44 (or other side edges) of the first tray 12 and thereby establish the location of the tray 12 in a substantially horizontal attitude spaced above the bottom 22 within the receptacle, thereby developing a chamber 25 within the receptacle and between the tray 12 and the bottom 22 of the receptacle 11. These ledges and the tapered profile of the receptacle also serve the function, among others, of allowing the stacking of several procedural trays 12 and 14 within the receptacle 11 (see FIG. 2) without the weight or pressure of the uppermost tray, 14, for example, from crushing or destroying the integrity of the underlying tray 12. This is accomplished by first placing loose items of supplies 23 and 27, for example, in the chamber 25, followed by the positioning in the receptacle of the first tray 12, such tray being of a cross-sectional size that it contacts and is supported by any two opposing ones of the several ledges 30A, 30B, 32A and 32B provided on the inner opposing walls 26 and 28 of the receptacle. Notably, by reason of the several ledges located at different heights above the bottom of the receptacle, the receptacle can accept any of several sizes and geometries of trays so long as the tray is of a size that two of its ends or edges can be lodged on any two of opposing ones of the ledges. This is true whether the selected opposing ledges be at different heights, thereby enhancing the ability of the receptacle to receive a substantial variety of tray sizes and shapes. Thereafter, other supplies and/or trays, such as larger trays 14, for example, are positioned within the receptacle above the first tray 12. Due to their larger cross-sectional size, the larger trays tend to wedge themselves within the receptacle at a location spaced above the first tray, thereby minimizing any adverse effect upon the first tray due to the weight of the second and other trays. Alternatively, a shelf may be substituted for the tray 12 as a means to support medical supplies held in the receptacle above the level of the ledges. Similarly, further shelves (not shown) may be frictionally wedged between the side walls of the receptacle at selected vertically spaced-apart levels to provide other support for supplies. Due to the tapered geometry of the depicted receptacle, preferably the heavier supplies are loaded toward the lower half of the receptacle to thereby develop the lowest possible center of gravity for the loaded receptacle. This provides protection against inadvertent tipping of the receptacle. As depicted in FIG. 8, the tapered geometry of the receptacle further provides for the nesting of multiple empty receptacles 11 and 13 for space-saving storage and other purposes.

Figure 6:
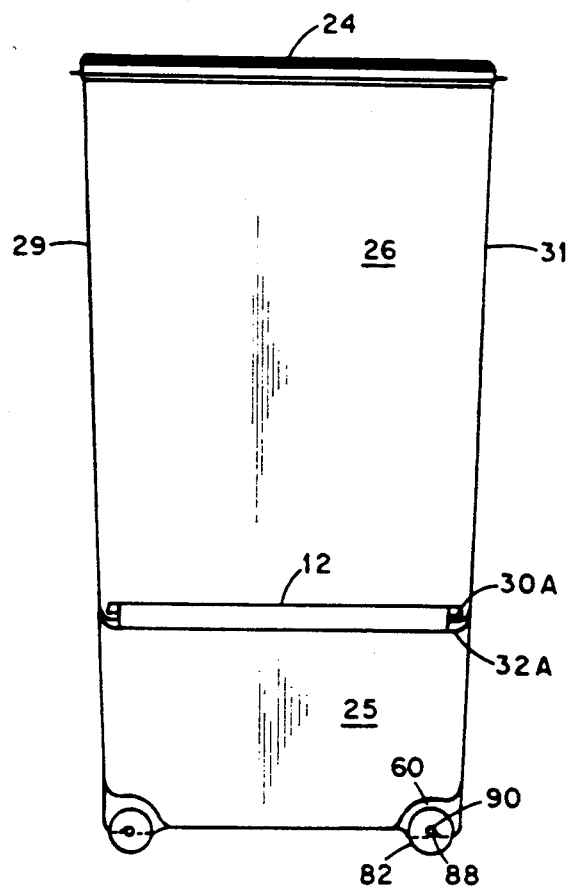
FIG. 6 is a cross-sectional view taken generally along the line 6—6 of FIG. 4.
Figure 7A:
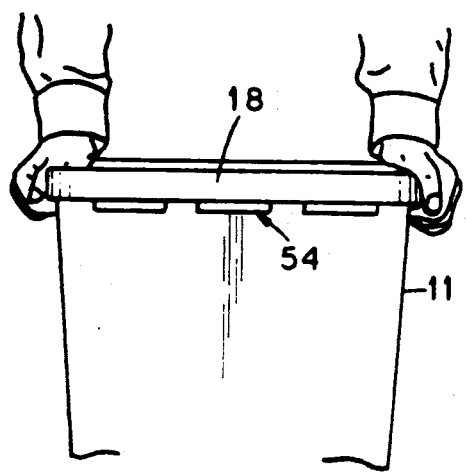
FIG. 7A-7D are a series of views of a portion of a receptacle of the type depicted in FIG. 1 and showing the steps to be followed in sealing the receptacle with its lid after used medical waste has been deposited therein.
Figure 7B:
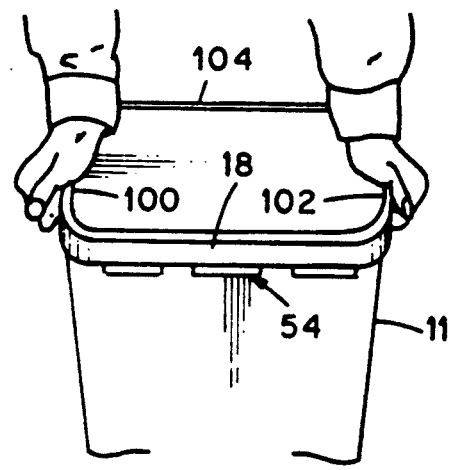
Figure 7C:
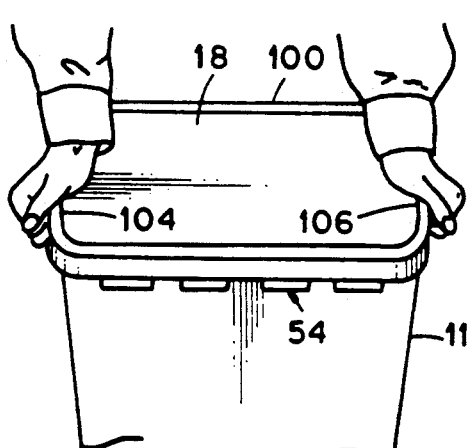
Figure 7D:
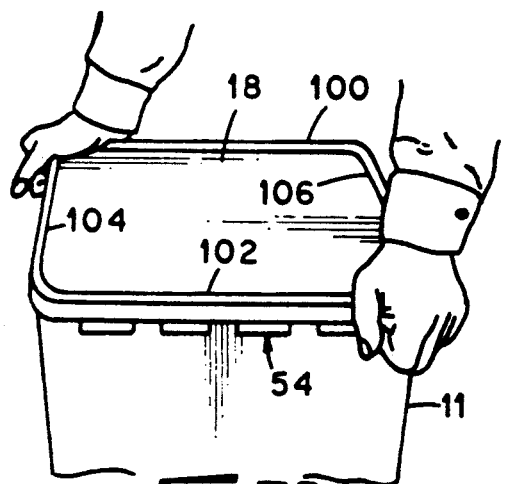

Also as depicted in FIGS. 4, 5 and 6, the preferred receptacle includes a circumferential rim 50 extending about the perimeter of the open top 24 of the receptacle 11. Such rim 50 is integrally formed with the top of the receptacle and projects generally perpendicularly from the side walls 20 of the receptacle (see also FIG. 5). A plurality of slots 52 are provided through the thickness of the rim 50 and are designed to receive therethrough a like number of locking lugs 54 that are provided on the lid 18. As seen in FIG. 4, the horizontal cross-sectional dimension of the receptacle 11 is generally rectangular with rounded corners. As noted, the area of such horizontal cross-section varies between the open top 24 and the bottom 22 thereof. Aside from the inward depressions that develop the ledge sets, the variation in cross-sectional area is substantially constant from the top to the bottom of the receptacle to provide a generally tapered narrowing of the receptacle from its open top 24 to the bottom 22 thereof. The ledges, as noted, provide stops and support for the tray of medical supplies. Only two sets of ledges are shown in the Figures, but additional sets of ledges may be provided as desired for like purposes.

As further depicted in FIGS. 4, 5 and 6, the receptacle 11 is provided with depressions in the bottom 22 thereof which define wheel wells 60, 62, 64 and 66. As best seen in FIGS. 5 and 6, each wheel well further includes means defining two open-ended slots 68 and 70 adapted to receive therein an axle 80 for a wheel 82 that is received into such well 60, one end 84 of the axle 80 being received in the slot 68 and the opposite end 86 of the axle 80 being received in the other of the slots 70. The elongated entrance portion 88 of the preferred slot 70 is slightly more narrow than the diameter of the axle received therein, with the closed end portion 90 of the slot 70 being circular in cross-section and of essentially the same diametral dimension as the axle 80. In this manner, the slot 70 is slightly distorted in the process of inserting the axle therein and thereafter rebounds to capture the axle in the closed end portion of the slot. Notably, in a preferred receptacle each wheel is mounted at a location on the bottom of the receptacle such that no portion of the wheel nor its mounting means extends outside the profile of the receptacle, other than from the bottom of the receptacle. Whereas the axles of the wheels of the depicted receptacle are fixed, it is to be recognized that caster-type wheels may be employed. In this manner, and as seen in FIG. 8, empty multiple receptacles 11 and 13 may be nested in one another for space-saving storage purposes. Each receptacle is provided with projections 90 and 92 on two opposite sides 26 and 28 thereof which serve as handles for facilitating the lifting the receptacles and further as delimiters of the extent of insertion of one receptacle within another when two or more such receptacles are nested. As seen in FIG. 8, the lower ledges 94 and 96 of the projections 90 and 92, respectively, of the first one 11 of a pair of nested receptacles contacts the upper edge 98 of the open top 24 of the second receptacle 13 immediately therebelow, thereby limiting the insertion of such first receptacle into the second receptacle.

Each receptacle 11 is provided with a lid 18 that is sealable over the open top of the receptacle. In FIGS. 1 and 3, such lid 18 is depicted in its position of closure of such open top. In FIG. 2, the lid 18 is shown inverted and in its position for temporarily closing the open top of the receptacle. In this position, the lid will not "seal" the open top, but will merely cover such open top. The inverted lid is placed over the open top of the receptacle after the medical supplies have been placed in the receptacle and removably secured in place, as by shrink wrap 97 disposed circumferentially about the lid 18 and the upper portion of the receptacle 11 (see FIG. 2). To this end, the lid 18 is formed with projections 19 on the top surface 21 thereof which are dimensioned so as to be received in the open top of the receptacle to align the lid on the receptacle. Thereafter the shrink wrap is applied to provide an effective temporary closure which maintains the lid in place and the contents within the receptacle and resists contamination as by dust or the like.

At the use site for the medical supplies, the shrink wrap is removed and the lid is lifted from the receptacle and placed aside for use in closing and sealing of the receptacle after the used waste medical supplies have been placed therein. FIGS. 7A–7D depict the preferred steps to be followed in closing and sealing the receptacle with the lid 18. In such Figures, after the lid is placed on the open top end 24 of the receptacle with the locking lugs 54 of the lid aligned with the slots 52 provided in the rim 50 of the top of the receptacle, pressure is applied to the long sides 100 and 102 of the lid to cause the lugs associated with such long sides to enter their respective slots and lockingly engage therewith. Thereafter, pressure is applied to the short sides 104 and 106 of the lid to likewise cause the locking lugs on such sides to enter and lockingly engage with their respective slots in the rim 50. Finally, pressure is applied to the corners of the lid to ensure complete engagement of all the locking lugs with their respective slots and full sealing of the lid with respect to the top of the receptacle. By reason of the design of the locking lugs and their respective slots, once the lid is properly secured in place, it can only be removed by destruction of the locking lugs or their slots or by the purposeful simultaneous application of diverse forces of a type which would result in physical damage or destruction of the lugs or slots. In this manner, the integrity of the seal of the receptacle is assured from the time that the receptacle is sealed at the use site and until it is ultimately disposed of as by incineration or otherwise.

Figure 9:
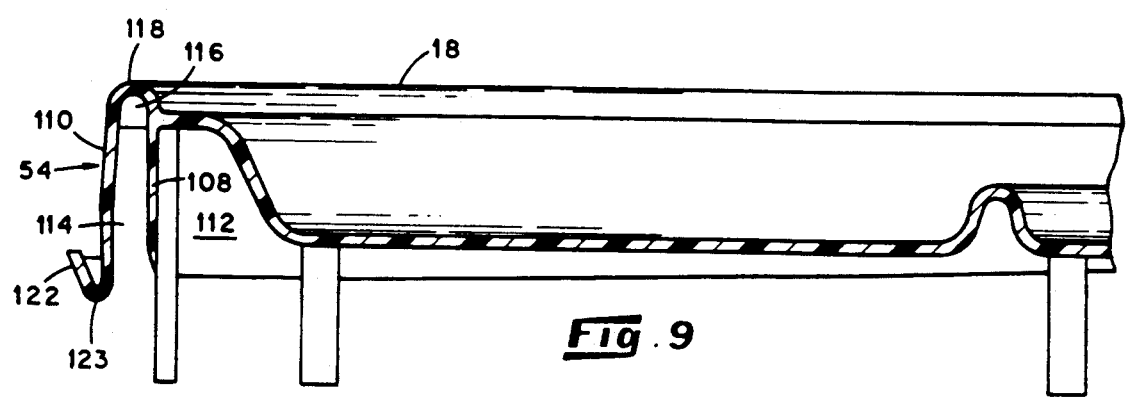
FIG. 9 is a sectional view of a portion of a lid of the type depicted in FIG. 1 and showing a typical locking lug.

Typical locking lugs 54 are depicted in several of the Figures. The detail of one suitable locking lug 54 is depicted in FIG. 9. With reference to such Figure, it is seen that such lug is of generally "U"-shaped geometry with one of the legs 108 of the "U" being defined by the wall 112 of the lid 18. The other of the legs 110 of the "U" is spaced outwardly from the lid wall 112 to define between the legs an open slot 114 which is suitably dimensioned to receive therein the top edge 24 of a receptacle (see also FIGS. 1 and 4). The length dimension of the open slot 114 is greater than that dimension of the upper edge of the receptacle to be received therein so that a sealing material 116, such as deformable resilient rubber or plastic, may be positioned in the closed end 118 of the "U" shaped slot and thereby be in position to bear against the top edge 24 of the receptacle top when pressure is applied to the lid to compress the resilient sealing material and permit the lugs to enter and lockingly engage their respective slots in the rim of the receptacle. To accomplish such locking relationship between the lugs and their respective slots, the lowermost end 123 of each leg 110 of each lug 54 is provided with an upturned extension 122 that projects outwardly and upwardly from the lowermost end 123 of the leg 110, hence outwardly and away from the lid and receptacle. The angle formed between the leg 110 and its extension 122, and the length of the extension are such that the extension will be deformed slightly when pressure is applied to the top of the lid as depicted in FIGS. 7A-7D, to cause the leg 110, and its extension 122, of the lug 54 to enter a slot 52. Upon passage of the extension through such slot, and release of the downwardly applied closing pressure upon the lid, the extension rebounds so that it can not be removed from the slot except by purposeful, and unlikely successful, reverse deformation of the lug and accompanying pressure applied to the lid to simultaneously compress the sealing material 116. Locking of the several lugs in their respective slots is further ensured by pressure exerted by the sealing material 116 contained in the slot 114 and which is substantially compressed in the process of applying closing pressure to the lid.

In the present system, as noted hereinabove, the empty receptacle is loaded with "fresh" medical supplies, as in the medical supply manufacturer's facility. Loading of the supplies into the receptacle involves placing first into the receptacle loose items of supplies, such as suction canisters or other items, such items preferably being of the type which require a higher degree of protection against crushing or other destructive forces encountered in shipping, storage, etc. Further, if possible those items first loaded in the bottom of the receptacle are the heavier items, thereby tending to lower the center of gravity of the loaded receptacle and reduce the likelihood of its being tipped over from its normal upright position. After the loose items have been loaded into the bottom of the receptacle, that is, in that lower portion of the receptacle below the horizontal location of the ledges 30A, 30B, 32A and 32B, a procedural tray is introduced into the receptacle with at least two of the opposite side edges of the tray resting on opposing ones of the ledges to thereby support the tray and its contents above the loose items in the bottom chamber of the receptacle. In lieu of using a tray, it is acceptable to employ a solid or perforated shelf that is dimensioned suitably to have opposing ones of its side edges received by opposing ones of the ledges to thereby position the shelf horizontally across the receptacle at the horizontal level of the ledges. Such shelf functions to support further loaded supplies above the loose supplies in the bottom of the receptacle and to protect those items in the chamber 25 as described with reference to a tray.

Following the positioning of the tray or shelf on the supporting ledges, further medical supplies are introduced into the receptacle as desired. Preferably the lighter weight supplies are the last ones to be loaded into the receptacle. As noted hereinbefore, multiple sets of ledges at different vertical levels within the receptacle may be employed to reproduce the protective effect afforded by the depicted sets of ledges and the accompanying use of a tray or shelf supported by such ledges. In this manner, multiple chambers substantially identical to chamber 25, may be provided within the receptacle.

After the receptacle is loaded with supplies, the lid 18 is positioned in an inverted attitude (see FIG. 2) in covering relation to the open end 24 of the receptacle. The lid 18 is provided with positioning lugs 103 at the corners of the lid which are receivable within the open top of the receptacle to thereby position the lid over the open top. Thereupon, a shrink wrap material 97 is placed in encircling relationship to the lid and the upper portion of the receptacle to provide for the temporary retention of the lid in place over the open top of the receptacle for preventing unauthorized access to the supplies contained within the receptacle and to protect the contents of the receptacle against dust, etc. When the receptacle is received at the use site, the shrink wrap is removed and the supplies are retrieved from the receptacle for use. The lid is temporarily set aside for use in later sealing the receptacle. The empty receptacle preferably is positioned near the use site to be available to receive waste developed in the course of the particular medical procedure and procedures. Such waste may include disposable items delivered initially in the receptacle, plus other waste items that may have been supplied from other sources. Such wastes commonly are contaminated with blood and/or other body fluids which may be infectious, and may comprise soft items such as sponges and hard or rigid items such as needles, disposable scalpels, blades, etc.

Upon completion of the medical procedure, or at such time as the receptacle becomes filled with waste, the medical personnel at the use site retrieve the lid for the receptacle, position it over the open top of the receptacle and lock it in its sealing relationship with the receptacle as depicted in FIGS. 7A-7D. As desired or required, appropriate labels 105 may be applied to the receptacle for identification and tracking purposes. The closed, sealed and labeled receptacle is thereafter transferred to an appropriate disposal facility. In all instances, the integrity of the closed and sealed container is maintained by the present system, thereby precluding loss of either solid or liquid contents of the receptacle and preventing access to the waste items without detectable destruction of the locking means between the lid and the receptacle. Further, those personnel required to handle the receptacle and its waste contents during the transport and disposal thereof are protected against contact by the contents, and especially against physical contact with blades, needles, etc. contained in the waste. Further, the preferred construction and fabrication materials of the receptacle and its lid protect against inadvertent, or even purposeful puncture of the receptacle between the time it is sealed and the time of its ultimate disposal.

The preferred method of disposal is by incineration. The present receptacle and its lid are amenable to incineration, producing little, if any, environmentally detrimental by-products. The preferred size of the receptacle is such that the entire receptacle may be loaded into commonly available incinerators.

Whereas specific embodiments and features of the invention have been described herein, it is not intended that such shall limit the invention other than as set forth in the claims appended hereto.

What is claimed:

1. A method for the delivery of disposable medical supplies to a use site and for the collection, transport and ultimate disposal of waste medical supplies comprising the steps of introducing into a rigid open receptacle including a lid means a quantity of said disposable medical supplies, said receptacle having walls and a bottom that are not incidentally penetratable by needles or surgical blades and which are liquid-impermeable, positioning said lid in a first covering relationship with said open receptacle to close and temporarily seal said receptacle with said supplies therein, said seal being sufficient to prevent the inadvertent loss of said medical supplies during normal transit from a manufacturing and/or distribution location to a use site for said medical supplies, associating identifying indicia with said receptacle, delivering said receptacle with its contents to a use site for said medical supplies without opening said sealed receptacle, at said use site, removing said lid from said receptacle to open said receptacle and removing said medical supplies from said receptacle to empty said receptacle, positioning said empty receptacle at a location at said use site suitable for the placement of waste medical supplies therein, placing waste medical supplies from said use site into said receptacle, positioning said lid in a second and different covering relationship with said open receptacle to thereby close and lockingly seal said receptacle with said waste medical supplies therein at said use site, said seal being such as to secure the receptacle against unauthorized entry into said receptacle, thereafter disposing of said receptacle and its contents at a location remote from said use site without opening of said sealed receptacle and in a manner which both destroys the recognizable identity of individual items of said waste medical supplies and which effectively destroys any infectious nature of said waste medical supplies and/or said receptacle.

2. The method of claim 1 wherein said waste medical supplies comprise disposable items that were originally delivered to the use site in said receptacle.

3. The method of claim 1 wherein said lid is reversibly positionable in closing relationship to said receptacle.

4. The method of claim 1 wherein said lid is secured in closing relationship with said receptacle by means of locking lugs that lockingly enter and engage respective open slots associated with said receptacle.

5. The method of claim 4 wherein said locking lugs engaging said open slots are not removable from said slots except by means of purposefully applied opening force sufficient to destroy said lugs and/or said slots.

6. The method of claim 1 and including the step of sterilizing at least certain of said medical supplies prior to their introduction into said receptacle.

* * * * *